United States Patent [19]

Kluft

[11] Patent Number: 5,004,802
[45] Date of Patent: Apr. 2, 1991

[54] 100KDA PROTEIN FROM BLOOD WHICH BINDS TO AND INHIBITS THE ACTIVITY OF PLASMINOGEN ACTIVATORS

[75] Inventor: Cornelis Kluft, Sassenheim, Netherlands

[73] Assignee: Nederlandse Centrale Organisatie Voor Teegepast-Natturwentenschappelijk Orderzoel, The Hague, Netherlands

[21] Appl. No.: 884,418

[22] Filed: Jul. 11, 1986

[30] Foreign Application Priority Data

Jul. 12, 1985 [NL] Netherlands ........................ 8502017

[51] Int. Cl.$^5$ ...................... A61K 37/02; C07K 15/06; C07K 15/14
[52] U.S. Cl. .................................. 530/380; 530/350; 530/381; 530/395; 530/412; 530/413; 530/417; 530/421; 530/829; 435/217; 435/215; 435/212; 435/216; 514/2; 514/8; 514/21
[58] Field of Search .............. 530/380, 350, 395, 381, 530/412, 413, 417, 421; 424/101; 435/215, 216, 212, 217; 514/2, 8, 21

[56] References Cited

PUBLICATIONS

Chemical Abstracts, vol. 94, No. 1, May 25, 1981, p. 431, Abstract No. 171576n, Takashi Okamura.
Chemical Abstracts, vol. 70, No. 15, Apr. 14, 1969, pp. 157–158, Abstract No. 66029t, G. J. H. Den Ottolander et al.
Chemical Abstracts, vol. 92, No. 5, Feb. 4, 1980, p. 337, Abstract No. 36736h, L. B. Nanninga et al.
Chemical Abstract, vol. 101, No. 19, Nov. 5, 1984, p. 424, Abstract No. 167884g, E. D. Sprengers et al.
*Proc. Natl. Acad. Sci. USA, vol. 80, May 1983, pp. 2956–2960*, D. J. Loskutoff et al., Cell Biology.
Chemical Abstracts, vol. 98, No. 9, Feb. 28, 1983, p. 405, Abstract No. 69433j, J. J. Emeis et al.

Primary Examiner—Esther L. Kepplinger
Assistant Examiner—Jeff P. Kushan

[57] ABSTRACT

A protein called PA binding protein has been isolated which binds specifically and reversibly to tissue plasminogen activator. The protein is characterized by a molecular mass of about 100,000 daltons, and electrophoretic mobility in agarose at pH 8.6 equal to that of plasma $\beta$-globulins and an isoelectric point of 6.5 to 7.0. The protein is thermostable up to at least 56° C. and is cleared from the circulation with a half life on the order of days.

1 Claim, 3 Drawing Sheets

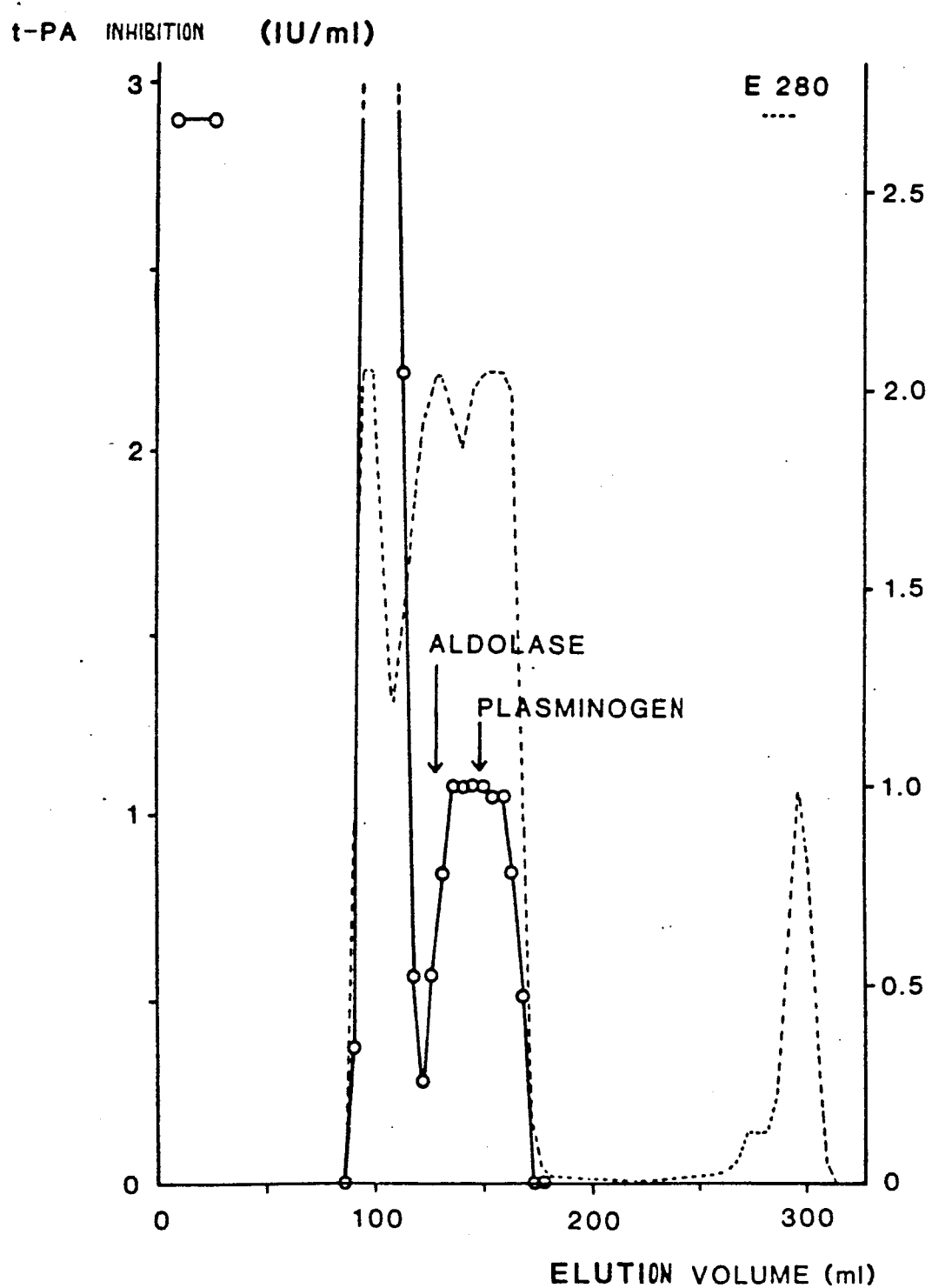

100KDA PROTEIN FROM BLOOD WHICH BINDS TO AND INHIBITS THE ACTIVITY OF PLASMINOGEN ACTIVATORS

BACKGROUND OF THE INVENTION

The present invention relates to a novel protein which has been identified in human blood and has been isolated therefrom. It is also present in the blood of other mammals, for example of the rat and of the rabbit. This novel protein appears to inhibit specifically plasminogen activator activities, namely those of tissue type plasminogen activator (t-PA) and urokinase. The protein has been called PA-binding protein (PA-BP).

It was known that plasma shows inhibition of t-PA which, for example, can be assayed with a PA-inhibition test (Thromb. Haemostas. 48, 266–269, (1982)). It was assumed that this inhibition was due to a well-characterized PA inhibitor (In: Recent Advances in Blood Coagulation, L. Poller, ed; Churchill Livingstone NY, Vol. 4, pages 11–33, (1985)) which had been found also in blood platelets, endothelium cell media and liver cell media.

BRIEF DESCRIPTION OF THE INVENTION

It was found that, in blood plasma, a second protein contributes to the inhibition of t-PA, and that this protein is not related to the PA inhibitor. The protein, which has a molecular mass of 100,000 (gel filtration) appeared to be a protein reacting reversibly with t-PA. This PA-binding protein (PA-BP) will be described hereinafter in more detail.

BRIEF DESCRIPTION OF THE FIGURES

FIG. 3 shows the results of gel filtration on PA-binding protein and PA-inhibitor.

DETAILED DESCRIPTION OF THE INVENTION

Figure 1:
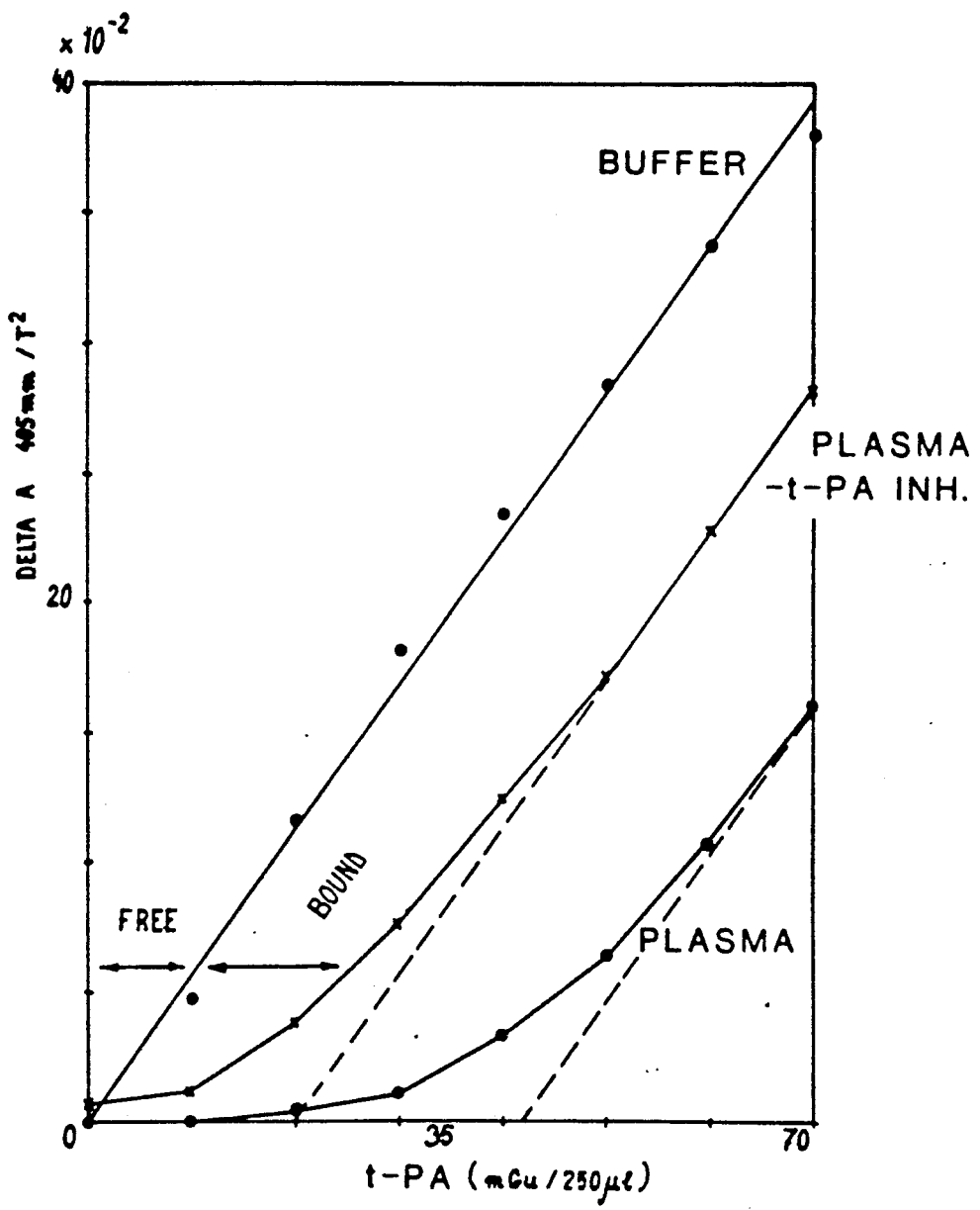
FIG. 1 illustrates graphically the results of a t-PA-inhibitor assay.

The conversion of fibrinogen to fibrin is an important biological process. Fibrin formation is crucial is hemostasis, but it is also an important aspect of other biological processes, for example in inflammatory and malignant diseases and in tissue repair processes. The degradation of fibrin deposits in the organism is catalyzed by the serine proteinase plasmin, and plasmin is formed from plasminogen under the influence of activators. Two types of plasminogen activators are known: of the tissue type (t-PA) and urokinase. It is known that the fibrin degradation is controlled by these plasminogen activators, by the plasmin inhibitors and by activator inhibitors.

The most important inhibitory protein controlling fibrinolysis via plasminos; activators, is PA inhibitor. Its inhibitor has been identified only since 1982-1983 and its activity may be assayed in a single manner by titration with t-PA which, in turn, can be assayed, for example, by means of the procedure according to Dutch patent application 8201987. Study of PA inhibitor has known that this protein can also be present in an inactive or latent form.

Further study of PA inhibitor has led to obtaining antibodies capable of neutralizing the activity of the inhibitor and which react with inactive forms. It was also found that the activity of PA inhibitor is unstable at 37° C. Measurements of the activity of PA inhibitors in plasma carried out during these studies led to the observation that part of the inhibition was not labile at 37° C. and that this part did not react with the antiserum against PA inhibitor. Further studies showed that a second PA inhibitory protein was involved.

The properties of PA-BP will now be discussed in more detail.

Human t-PA contains two homologous kringle structures, a domain homologous to a part of the epidermal growth factor, a domain homologous to the finger structure of fibronectin and a light chain domain with the serine-containing active centre. These domains are considered to play a role in binding ligands, proteins and cellular structures, which bonds are essential for the regulation of the biological function of t-PA. The related plasminogen activator, urokinase, has a kringle and a light chain with the active centre.

The control of the availability of t-PA for fibrinolysis is, also in view of the large number of domains in the molecule, extremely complicated.

In the coagulation of fibrinogen the t-PA is incorporated into the clot. The availability of t-PA in the circulation or its rapid recrutation from the endothelium cells of the vascular wall at the time of clot formation is an essential parameter for fibrinolysis. Insufficiency in this respect means a thrombotic diathesis; excess of t-PA means a hemorrhagic diathesis.

The fibrin-directedness of the activity of t-PA is important, in contradistinction to the activity of urokinase and streptokinase (a bacterial product), with which the binding to fibrin provokes a two orders of magnitude stimulation of the t-PA activity. This property of t-PA is used in the application of t-PA as a thrombolytical agent. Amounts of urokinase and streptokinase which are necessary for clot dissolution in thrombosis and, for example, heart infarction, also give considerable effects in the circulation where plasmin formation takes also place, and the plasmin provokes undesirable proteolysis resulting in an increased bleeding risk. The activity of t-PA outside the clot is substantially lower.

The control of the availability and the activity of t-PA is, among others, also effected by inhibition, namely by the PA inhibitor. In the circulation, PA inhibitor contributes to the inactivity of t-PA and to limitation of undesirable proteolysis by plasmin to be formed. To that end it forms very quickly a reversible complex with t-PA, which complex is converted slowly (half-life about 0.5 hour) into an irreversible complex in which t-PA is inactive. The blood levels of PA inhibitor are very variable (from 0 to 18 IU/ml) and this action of PA inhibitor is, therefore, variable as well. Moreover, in the clotting process at 37° C., PA inhibitor is inactivated apparently spontaneously (half-life 80–100 minutes) by active protein C and thrombin. The newly found component, PA-BP, has a much more stable plasma concentration, is stable and is, therefore, an important continuous factor in the prevention of t-PA activity in the circulation.

In view of its lability, PA inhibitor is only temporarily present in the clots formed and is important only for the temporary stabilization of the clot by inhibition, in the clot environment, of plasminogen activators which, among others, arrive from outside. The PA-BP is permanently present and is of importance for the longer term control of the PA activity.

In thrombolytic therapy with PA high dosages of t-PA appear to be necessary for obtaining the desired thrombolysis, which dosages are far higher than the concentrations of PA inhibitor and PA-BP, resulting in systemic effects. The dosages are also high so as to compensate for the very quick clearing of t-PA by the liver (half-life of minutes). Experiments in rats have shown that preincubation of t-PA with plasma containing only PA-BP resulted in a decrease by a factor four in the clearing of the labelled t-PA.

The new component, PA-BP, shows its activity in the t-PA inhibition test as an inhibition of the plasminogen activating activity of t-PA. Further analysis shows, however, that also the reaction of t-PA with PA inhibitor is inhibited, just as the reaction with other plasma inhibitors which are capable of irreversibly neutralizing t-PA. Therefore, PA-BP should be seen as a protective factor which, on the one side, protects t-PA against inactivation by inhibitors and, on the other side, protects plasminogen against inactivation with undesirable plasmin formation. Consequently, PA-BP is a safe carrier for t-PA in the circulation. Binding of t-PA to fibrin in clotting is not inhibited. These reasonings are equally valid for urokinase, when adapted to its specific properties.

It may be derived from these data that PA inhibitor and PA-BP play different roles in the control of the availability of t-PA and that the roles may vary dependent on the conditions. There is still only fragmentary knowledge about which of the domains of t-PA are involved in the interaction with fibrin, plasminogen, PA inhibitor and PA-BP. The binding of fibrin is assumed to relate to the finger domain. The plasminogen activation is intact if only the light chain of t-PA is studied. The interaction with PA-BP was found to be intact when a t-PA mutant obtained by recombinant DNA techniques was studied, in which the N-terminal parts inclusive of kringle 1 were lacking. The light chain lacking also kringle 2 appeared to have no interaction with PA-BP, and this was also not the case with t-PA having a DFP-inactivated active centre. Apparently, kringle 2 and the active centre of t-PA are involved in the interaction with PA-BP. Study of urokinase with and without its kringle showed that the presence of the kringle was not essential for interaction with PA-BP, but the active center was, because prourokinase did not show any interaction. So, at least the active centre of the plasminogen activators is of importance for the interaction with PA-BP.

Assay of PA-BP can be carried out with the assay method for PA inhibitor, in which the influence of any PA inhibitor present in the sample has been destroyed by addition of IgG against this inhibitor or by preincubation of the sample during a suitable period of time, for example 37° C., by which time PA inhibitor is inactivated exclusively. In this assay method soluble stimulator or fibrin monomer may be used. The dosage-response curve for the assay is linear and the activities of the PA inhibitor and PA-BP are additive.

The interaction between t-PA and PA-BP shows reversable kinetics which, in a reciprocal plot of free against bonded t-PA shows an apparent dissociation or inhibition constant of 1-5 picomolar. The reversibility of the interaction between t-PA and PA-BP is further supported kinetically by the observation that the amount of remaining t-PA (in spite of excess of PA-BP) remains constant during hours and that, on dilution, the equilibrium shifts in the direction or higher dissociation with a higher percentage of free t-PA. Another observation showing the reversible character of the t-PA with PA-EP was made by addition of t-PA or urokinase to plasma. When an excess of t-PA or of urokinase is added to plasma, PA-BP activity is no more detectable. It appears that after incubation at 37° C. of such a mixture the activity of PA-BP returns after some time. Apparently, in this case PA-BP is neutralized initially and t-PA and UK are bonded, but on a longer term the added t-PA and urokinase are irreversibly inactivated in plasma by slowly acting plasmatic inhibitors, such as alpha-2-antiplasmine. This shows that PA-BP can not be neutralized permanently by plasminogen activators.

In plasma, the activity of PA-BP is stable when incubated at 0° to 56° C. for periods of up to a week. At 37° C. PA inhibitor activity disappears with a half-life of 80-100 minutes. After a suitable multiple of this half-life, for example after incubation overnight, plasma contains exclusively the PA-BP activity. The inactivation of PA inhibitor is strongly dependent on the temperature with a Q 10 of 5, the incubation at higher temperatures proceeding much more rapidly. In plasma, after immune precipitation with IgG against PA inhibitor, a PA inhibition remains which is thermostable and is quantitatively identical to PA-BP. The same activity, identical to PA-BP, remains after addition of an excess of PA inhibitor IgG in the assay method for t-PA inhibition. The PA-BP activity remaining after incubation of plasma at 37° C. overnight is insensitive to inhibition of excess IgG against PA inhibition. The activity of PA-BP is insensitive to the addition of EDTA. The placenta inhibitor of plasminogen activators is not found in normal plasma and the activity of PA-BP is not neutralized by antibodies against placements inhibitor which, under the same conditions, do inhibit the placents inhibitor activity.

The identify of PA-BP with known inhibitors showing interaction with the fibrinolysis components is excluded in view of the concentration in plasma which is not so low for any of the known inhibitors except PA inhibitor. PA-BP is normally present in antiplasmin deficient plasma. Purified tetranectin (Dutch patent application 8501682) does not show inhibition of t-PA. Plasminogen and fibrinogen can be removed from plasma without destroying PA-BP activity. Alpha-2-macroglobuline and C1-inactivator show up at a position clearly different from that of PA-BP in gel filtration of plasma. In fibroblast medium in which the protease nexin is present, no PA-BP was detected.

In plasma, PA-BP may be separated from PA inhibitor by gel filtration. PA inhibitor moves to a position of high molecular weight and PA-BP runs approximately concurrently with plasminogen at a molecular weight of 100,000. Both of the peaks comply with the characteristics that PA inhibitor can be neutralized with the antiserum and is temperature-labile whereas PA-BP is insensitive to the antiserum and is temperature-stable. This is in agreement with the fact that gel filtration of plasma which has been preincubated during 24 hours at 37° C., yields PA-BP only.

PA-BP can be precipitated with ammonium sulphate between 30 and 50% saturation and with polyethylene glycol between 0 and 9%. PA-BP is not bonded to lysine-agarose, so that plasma may be made plasminogen-free by using this column without loss of PA-BP. PA-BP does not couple to a column of DFP treated t-PA showing that an intact active center of t-PA is essential for the interaction with PA-BP.

In electrophoresis in agarose, PA-BP gives a single activity peak running concurrently with the β-globulins of plasma. In iso-electric focussing PA-BP appears at pH 6.5-7.0, which is in agreement with the electrophoretic mobility in the agarose.

PA-BP, in contrast to t-PA inhibitor, was not found in measureable amounts in conditioned media of cultures of endothelial cells, HEP G2 cells and of heptocytes. Also in highly concentrated media (20×) obtained by freeze-drying no measurable amounts of PA-BP could be detected.

PA-inhibitor was detected in triton X-100 extracts of blood platelets, but PA-BP was not, as appeared clearly from the fact that all of the PA inhibition could be inhibited with the antiserum against PA inhibitor.

In pooled normal plasma a PA-BP concentration of 5 IU/ml was determined which, with a molecular weight of 100,000 corresponds to the low value of 10 ng/ml or 0.1 nmole/l. This is a 10-100-fold excess with respect to free t-PA in a plasma obtained under resting conditions. With an inhibition/dissociation constant of t-PA and PA-BP of 1-5 pmolar this means that essentially all of the t-PA exists in complex with PA-BP. In healthy individuals a fairly constant (standard deviation 15%) PA-BP concentration was found; this is in contrast with the large interindividual variation of PA inhibition. When it became clear that, in the PA inhibitor assay in plasma, the PA-BP value has to be subtracted from the total so as to measure specifically PA inhibitor, the interindividual variation of PA inhibitor became still more striking, and many cases of essentially zero PA inhibitor activity were found. Apparently, PA inhibitor is frequently not detectable in plasma.

Variations in PA inhibition in plasma now may be due to the two separate components. It was found, however, that the variations were mainly due to PA inhibitor and that, for example, the daily rhythm and the acute phase reaction of the inhibition were due to the PA inhibitor, whereas the PA-BP was constant or showed limited fluctuation.

Also in animal plasmas, such as of the rat and the rabbit, a thermostable component was found, comparable with PA-BP. Strong fluctuations in PA inhibitor were seen, for example on injection of endotoxin, whereas PA-BP remained constant.

After infusion of rat plasma having a high level of PA inhibitor (obtained by injection of endotoxin and blood sampling after 4 hours in another animal) in rats it was observed that the PA inhibitor showed a rapid clearing having a half-life of 3-4 minutes, whereas the level of PA-BP which was also increased by the infusion, hardly decreased during the observation period. This suggests an order of magnitude of days for the half-life or PA-BP. This means that the stable plasma concentrations of PA-BP also during and after the circulation of high amounts of t-PA, such as after DDAVP infusion, are not obtained by rapid synthesis. It is to be assumed that when t-PA is rapidly cleared from the circulation via the liver the t-PA is dissociated from the PA-BP.

Summarizing, the properties of the novel protein according to the invention, called PA-binding protein (PA-BP), are the following:

PA-BP is a plasma protein having a molecular mass of 100,000 as estimated by gel chromatography on Ultrogel ACA 44.

The electrophoretic mobility is agarose-electrophoresis is equal to that of plasma β-globulins.

The isoelectric point is 6.5-7.0.

PA-BP is thermostable up to at least 56° C. for days.

PA-BP does not bind to fibrin and does not inhibit the binding of t-PA to fibrin. PA-BP does not contain sugar residues which bind the concanavaline A.

PA-BP inhibits the t-PA activity with an apparent inhibition constant of 1-5 picomolar. This inhibition is reversible on a short and long term and also inhibits the inactivation of t-PA by other inhibitors.

PA-BP interacts with urokinase, not with prourokinase.

For the interaction with PA-BP an active center of the plasminogen activators is necessary.

In the interaction with PA, kringle 2 is involved.

PA-BP is different from PA inhibitor according to immuno-logical criteria and protein-chemical characteristics, and as far as distribution in the body is concerned.

PA-BP has a constant plasma concentration of about 10 ng/ml, coupled with a slow clearing of days from the circulation, and does not occur in measureable amounts in platelets and culture media of endothelial cells and hepatocytes.

The invention relates to PA-BP having the above mentioned properties. The invention also relates to processes for the preparation of PA-BP. In the first place PA-BP can be obtained from blood or from blood fractions of mammals, such as of humans or of the rabbit or the rat, by means of usual protein purification techniques adapted to the properties of the protein.

The invention also comprises PA-BP prepared from cell cultures or by means of micro-organisms or other host organisms modified by means of recombinant DNA techniques.

The purification of PA-BP may be carried out by affinity chromatography on a column with coupled plasminogen activator or with mutant t-PA in which the N-terminal parts, inclusive of one kringle, may be absent. The affinity chromatography may be carried out e.g. in the absence of plasminogen and may be completed with traditional separation techniques which are adapted to the properties of the protein. The active with of the plasminogen activators should be intact or marginally modified.

Further, the invention relates to detection and assay methods in which pretreatment of the sample or addition of PA inhibitor antibodies make existing methods specific. Also, the invention relates to processes for making existing PA inhibitor assay methods specific for this particular factor. All of the known assay methods for PA inhibition in plasma and other samples may be used herein. Thus, the assay method is made specific for PA-BP by addition of PA inhibitor antibodies or by preincubation of the sample during a suitable period of time, for example during at least 10 hours at 37° C. so as to inactive the PA inhibitor. The specific contribution of PA inhibitor is calculated as the activity neutralized by the antibodies or inactivated by the preincubation.

PA-BP is present in human plasma in an average concentration of 0.1 nmole/l. This average has been determined in normal healthy volunteers. The PA-BP concentration does not change during the day (0900-1500 hours) and is not strongly different in patients with an acute phase reaction or sepsis. The PA-BP level is not lowered by temporary increase of circulating t-PA, such as by DDAVP-infusion.

PA-BP controls the availability of t-PA and urokinase by reversible binding of the plasminogen activators in a specific way, in which the binding of t-PA to fibrin is not inhibited, but the activity of plasminogen activators is inhibited in absence of polymerized fibrin and in the presence of fibrin and fibrinogen fragments or decomposition products thereof. Plasminogen activators are protected against inactivation by other processes.

In view of this role of PA-BP, the PA-BP may be used as a fibrinolysis controlling agent. Due to the slow clearing from the circulation a low amount of material can effect a substantial increase of the plasma level for a long period of time. The product may be of value for lowering systemic effects of plasminogen activators. It may be valuable as an additive to t-PA or urokinase in thrombilitic therapy and may lower systemic effects as compared to thrombilitic effects. It may be valuable in repressing fibrin-independent activities of plasminogen activators, such as in extra-cellular decomposition, in disseminated intravascular clotting.

Therefore, the invention also relates to pharmaceutical compositions containing PA-BP as an active component.

The following examples serve as illustration of the invention. The materials and methods used in the examples are the following:

Ultrogel ACA 44 was from LKB (Sweden).

Stimulator was prepared from fibrinogen by treatment with cyanogen bromide as described by Verheijen et al (Thromb. Haemostas. 48, (1982) 266–269).

S2251. This chromogeneous plasmin substrate having the formula H-D-Val-Leu-Lys-p-nitroanilide.2HCl was obtained from the film Kabi, Molndal, Sweden.

Plasminogen. Plasminogen was isolated from Cohn's fraction III by affinity chromatography on lysine-eupergit.

t-PA. One-chain and two-chain t-PA were isolated from cell culture media of the Bowes melanoma cell line as described in Kluft et al. In: Advances in Biotechnological Processes vol. 2 (Mizrahi, A. v. Wezel AL, eds) New York: AR Liss, 1983, pages 97–100. t-PA was coupled to sepharose according to the instructions of the firm Pharmacia for CNBr- sepharose. t-PA was inactivated by treatment with diisopropyl fluorophosphate (1 mM). The light chain of t-PA containing the active centre was obtained by reduction of two-chain t-PA, reoxidation and separation by means of gel filtration. A mutant t-PA lacking the finger, growth hormone, and N-terminal kringle-domains was prepared by recombinant DNA manipulation of the c-DNA ending for melanoma t-PA. Expression of the mutant was obtained in CHO (Chinese Hamster Ovarium) cells.

Urokinase was obtained as a mixture of the high and low molecular forms from Leo, Ballerup, Sweden and as the low molecular form from the firm Abbott.

Pro-urokinase was purified from monkey kidney cell cultures by adsorption to a column with IgG against urokinase.

IgG against PA inhibitor. PA inhibitor was isolated from endothelial cell media as described by Van Mourik et al (J. Biol. Chem. 259, (1984), 14914–14921). An antiserum was generated by immunisation of rabbits, and the IgG's were purified with Protein A Sepharose (Pharmacia, Uppsala, Sweden).

Endotoxin, Escherichia coli (serotype 0128:B12) was from Sigma, St. Louis U.S.A..

Wistar rats were obtained from the Centraal Proefdierenbedrijf TNO, Zeist and tests were carried out under Nembutal anaesthesis (60 mg/kg ip).

Endothelial cells were isolated from umbilical cord vessels by collagenase fermentation, and were cultured to confluence on fibronectin coated discs in Dulbecco's modified Eagles medium, without serum additions. Cells of the permanent hepatoma cell line HEP G2, hepatocytes and fibroblasts were cultured under standard conditions in serum-free media.

Plasma was obtained from donor blood and was stabilized with 0.10 volume of a solution containing 0.11M sodium citrate.

Gel filtration on Ultrogel ACA 34. This was carried out in a column of 275 ml equilibrated and packed with 0.10 M Tris HCl buffer, pH 7.4 and 0.05M NaCl. The column was calibrated by using various marker proteins and by internal calibration via measurement of the plasma plasminogen according to the streptokinase activation method of the firm Kabi, Molndal, Sweden.

The isoelectric focusing was carried out in rods of polyacrylamide gels which, after electrophoresis, were cut into slices. The pH-gradient was measured by extraction of the slices in water. The t-PA inhibition was measured after extraction of the slices in test buffer of the inhibition assay method. The pH-gradient of 3.5–9.5 was studied.

t-PA assay. t-PA is incubated at 25° C. in 0.25 ml Tris-HCl buffer (0.10 M, pH 7.5), containing 0.13 $\mu$M plasminogen, 0.1% (v/v) Tween 80, 0.12 mg/ml fibrinogen fragments (stimulator, or fibrin monomer) and 0.30 mM chromogeneous plasmin substrate (e.g. S2251). The light absorption at 405 n, is measured after various incubation periods. The assay is carried out in a microtiter plate having 96 wells and with a Titertek test apparatus (Flow, Irvin, U.K.). The increased light absorption divided by the square of the incubation time is proportional to the activator concentration. The t-PA activity is expressed in International Units according to the First International Standard of the WHO, code 83/517.

EXAMPLE I

The t-PA-inhibitor assay is carried out as a titration of an inhibitor containing sample, for example plasma, with a t-PA series. The t-PA activity is assayed with the above mentioned t-PA assay method.

FIG. 1 shows how addition of 20 $\mu$l plasma gives a curve in the test which, on extrapolation to the X-axis, shows the amount of inhibition expressed as the amount t-PA neutralized. FIG. 1 also shows that plasma which has been incubated at 37° C. overnight, shows less inhibition. This residual inhibition cannot be inhibited with immunoglobulins against PA inhibitor isolated from endothelial medium. These immunoglobulins do have effect on fresh plasma and decrease the inhibition of t-PA to the level of the incubated plasma. Therefore, this curve is provided with the indication plasma -(minus) t-PA inhibitor.

EXAMPLE II

Thermolability of PA inhibitor

Figure 2:
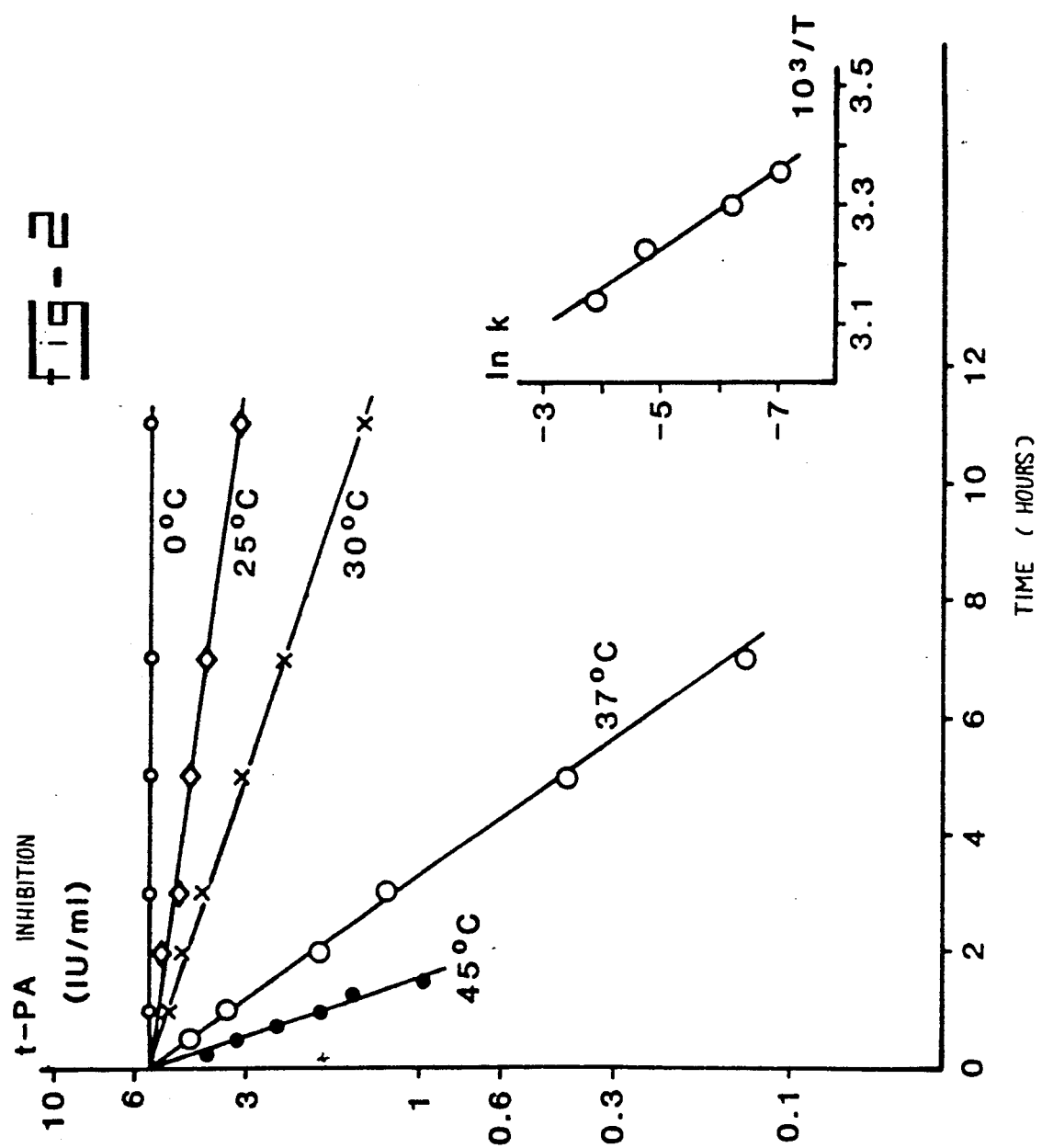
FIG. 2 illustrates graphically the thermolability of t-PA-inhibitor.

FIG. 2 shows that the t-PA inhibitor activity of PA inhibitor in pooled normal plasma decreases on incubation at temperatures higher than 0° C. The inhibition by PA-BP has been subtracted. The inactivation rate (k) is highly temperature-depending with a factor 5 increase per 10° C. temperature increase (inset). It was observed that the residual inhibition of PA-BP remains stable for at least one week and up to a temperature of 56° C. in any case. Up to now the same inactivation rate of PA inhibitor was found in all individual plasma's.

EXAMPLE III

Inhibition kinetics

The apparent inhibition constant may be obtained from results, such as in FIG. 1, by plotting the reciprocal values of free and bound t-PA. Extrapolation of these linear curves shows an axis section on the X-axis representing the same value of 1–5 picomolar for total plasma, endothelial cell medium and incubated plasma (PA-EP) in all cases. When a mixture of t-PA and incubated plasma or purified PA-EP is assayed in different dilutions, a different percentage of free t-PA is found. For example, in the dilution of t-PA deficiency 38%, 33% and 22% of free t-PA was found at dilutions of 1 to 10, 1 to 3 and undiluted, respectively. This suggests reversible complex formation.

EXAMPLE IV

Reversible binding of PA and PA-BP

Addition of a four-fold excess of t-PA or urokinase with respect to the total inhibitor capacity of normal plasma showed, on assay, that all of the inhibition with respect to t-PA was neutralized in the inhibitor assay. After inhibition overnight of the mixtures at 37° C. inhibition was again measurable, which was quantitatively equal to the PA-BP activity, and remained stable. Apparently, as is known, t-PA and urokinase had been inactivated slowly in the plasma medium by other protease inhibitors present in large amounts, and PA-BP was released again and, apparently was not neutralized irreversibly.

EXAMPLE V

PA-BP assay in plasma

To this end, plasma is pretreated by incubation during a suitable period of time (two hours at 45° C. or overnight at 37° C.) so as to inactivate PA inhibitor. Then the inhibition is assayed according to the above mentioned t-PA inhibitor assay method. This method appears to work also for plasma of e.g. the rat and the rabbit, in which PA-BP was also found. Namely, the incubation technique is also suitable for samples containing considerable amounts of t-PA, such as after stimulation of fibrinolysis and by infusion of t-PA, in which the interferring PA activity also disappears by the incubation (see example IV). As an alternative of human material substantially free of t-PA or urokinase, without pretreatment of plasma, the t-PA inhibitor assay is carried out with addition to the assay system of an excess of IgG against the endothelial PA inhibitor. This is $\geq 1$ mg/ml IgG of the anti-serum used.

EXAMPLE VI

PA-BP in media and in clinical examples

It was determined with the PA-BP assay method that the amount of PA-BP present in plasmas of normal donors is fairly constant (standard deviation 15%) and is equivalent to 5 IU t-PA/ml. No variation was seen during the day between 0900 and 1500 hours and in patients having a clear acute phase reaction with a high PA inhibitor level, such as after multiple trauma (two or more large bone fractures). During DDAVP infusion, PA-BP appears to be neutralized only temporarily by the circulating t-PA, and is always normally detectable after incubation of plasma. Injection of endotoxin (10μg/kg) in rats led, after 4 hours, to excessively high inhibition values in plasma (up to 1500 %) which, however, were entirely due to PA inhibitor; PA-BP remained unchanged. In endothelial cell culture media and HEP G2 cells all of the t-PA inhibition can be inhibited with IgG against PA inhibitor. Also, 20-fold concentration of the media did not show a measurable PA-BP content. Triton X-100 extracts of blood platelets pelleted from blood showed a t-PA inhibition which could be inhibited entirely with IgG against PA inhibitor. Fibroblast medium containing the protease nexin did not show any PA-BP activity. PA-BP was not found in euglobulin fractions of plasma.

EXAMPLE VII

Specificity of PA-BP

The t-PA-inhibitor assay method was used to find out which components added to a plasma containing only PA-BP, influenced the PA-BP activity. In this way it was found that addition of 10 ng/ml Leo urokinase or Abbott urokinase neutralized the PA-BP activity for 50% suggesting an equally strong binding as for t-PA. Prourokinase purified from monkey kidney cells (14 ng/ml) and present in human fibroblast medium (100 ng/ml) did not show any effect. The same experiment for t-PA showed that DFP-inactivated t-PA (100 ng/ml) and the isolated active light chain of t-PA (10 ng/ml) had no effect whatsoever.

The t-PA of the assay procedure was replaced with a deletion mutant t-PA obtained by recombinant DNA manipulation. This mutant did not contain the finger, growth hormone and kringle-1 domains. It appeared that the PA-BP activity could still be assayed normally with this. Apparently, the interaction between PA-BP and plasminogen activators is primarily dependent on an intact active center, and with t-PA, also on kringle 2.

EXAMPLE VIII

Gel filtration of PA-BP

Gel filtration of 5 ml of plasma on Ultrogel ACA 44 shows a separation of PA inhibitor and PA-BP. The two peaks in FIG. 3 were identified by their thermolability. PA-BP appears to chromatograph at a position corresponding to a molecular weight of 100,000, close to plasminogen (90,000) and after aldolase (147,000).

EXAMPLE IX

Fibrin binding of t-PA t-PA was added to plasma which showed PA-BP activity only, due to incubation at 37° C. t-PA was added in amounts equivalent to that of the PA-BP capacity and twice that amount. The plasma was clotted by addition of calcium chloride and thrombin, and the clot formed was removed. In the serum formed the same amount of PA-BP could be assayed in the control without t-PA, and in the two plasmas with t-PA, namely the same amount as present in the starting plasma. This shows that t-PA binding to the clot has taken place without hindrance by PA-BP.

EXAMPLE X

Protection of t-PA against inhibition

Various incubation times were studied in the PA inhibition assay method under various conditions. In plasma containing only PA-BP it was observed that the t-PA activity remains stable during 5 hours at 25° C. with t-PA concentrations lower than the PA-BP level.

Above the equivalence point, t-PA is inactivated by plasmatic inhibitors with a half-life of about 1 hour. It is remarkable that the inactivation stops at about the equivalence point. Apparently, PA-BP protects t-PA against inactivation by plasma inhibitors. A similar test in which serum-free medium of cell cultures is used, in which only PA inhibitor is present, shows that the t-PA activity is inactivated slowly and irreversibly (half-life 2.5–3 hours). In plasma, in which both PA-BP and PA inhibitor are present, t-PA is slowly inactivated with a half-life of 2.5–3 hours above the equivalents point of PA-BP, and the t-PA activity is stable below this equivalence point. Apparently, PA-BP also protects against the activity of PA inhibitor.

I claim:

1. A protein called plasminogen activator binding protein purified so as to be free from contamination with materials that interfere with the plasminogen activator binding activity of the protein, having at least the following properties;
   (a) it has a molecular mass of about 100,000 daltons as determined by gel chromatography on ULTROGEL ® ACA 44;
   (b) it has an electrophoretic mobility in agarose at pH 8.6 equal to that of plasma $\beta$-globulins;
   (c) it migrates to an isoelectric point of from 6.5 to 7.5;
   (d) the protein binds specifically and reversibly to urokinase having a free active center;
   (e) the protein binds specifically and reversibly to t-PA having a free active center and specific Kringle-2; and
   (f) the protein is thermostable so that it remains its plasminogen activator binding activity when heated to up to at least 56° C.

* * * * *